United States Patent [19]

Araki et al.

[11] Patent Number: 5,556,624
[45] Date of Patent: Sep. 17, 1996

[54] METHOD OF IMMUNOPOTENTIATING AND PROTECTING AN ANIMAL FROM E. COLI INFECTIONS USING A COMBINATION OF ROSA ROXBURGHII, ARTEMISIAE ARGYI FOLIUM AND BRASSICA OLERACEA VAR. CAPITATA L.

[75] Inventors: Seiichi Araki; Mamoru Suzuki; Masatoshi Fujimoto, all of Ibaraki; Tadashi Ueki, Tokyo, all of Japan

[73] Assignee: Eisai Co., Ltd., Tokyo, Japan

[21] Appl. No.: 333,079

[22] Filed: Nov. 1, 1994

Related U.S. Application Data

[62] Division of Ser. No. 285,980, Aug. 4, 1994, which is a division of Ser. No. 133,708, Oct. 7, 1993, abandoned.

[30] Foreign Application Priority Data

| Oct. 7, 1992 | [JP] | Japan | 4-291995 |
| Oct. 7, 1992 | [JP] | Japan | 4-291996 |
| May 25, 1993 | [JP] | Japan | 5-144345 |
| Jul. 30, 1993 | [JP] | Japan | 5-206808 |

[51] Int. Cl.⁶ .................................................. A61K 35/78
[52] U.S. Cl. ........................................ 424/195.1; 424/93.7
[58] Field of Search ..................... 514/867; 424/195.1, 424/93.7

[56] References Cited

U.S. PATENT DOCUMENTS 3,108,040  10/1963  Folkers ..................................... 167/55

OTHER PUBLICATIONS

Yoshida, T. et al, "Chem. Pharm. Bull." vol. 35, #5, pp. 1817–1822 (1987).
Shabana, M. M. et al., "Egypt. G. Pharm. Sci," vol. 19(#1–4), pp. 271–280, 1978.
Preobrazhenskaya, M. N. et al.," Pharmac. Ther." vol. 60, 1993, pp. 301–313.

*Primary Examiner*—Michael G. Wityshyn
*Assistant Examiner*—Kristin Larson
*Attorney, Agent, or Firm*—Flynn, Thiel, Boutell & Tanis, P.C.

[57] ABSTRACT

A method for immunopotentiating and protecting an animal from an infection caused by *E. coli* is described. The method comprises administering a composition containing *Rosa roxburghii, Artemisiae argyi folium*, and *Brassica oleracea* var. capitata L. to the animal.

5 Claims, No Drawings

5,556,624

METHOD OF IMMUNOPOTENTIATING AND PROTECTING AN ANIMAL FROM E. COLI INFECTIONS USING A COMBINATION OF ROSA ROXBURGHII, ARTEMISIAE ARGYI FOLIUM AND BRASSICA OLERACEA VAR. CAPITATA L.

This is a division of Ser. No. 08/285,980, filed Aug. 4, 1994, which is a division of Ser. No. 08/133,708, filed Oct. 7, 1993, now abandoned.

BACKGROUND OF THE INVENTION

1. Field of the Invention

The present invention relates to a medicinal agent or food which potentiates the immune system of an animal, including a human being, to thereby protect the animal from infection, and a feed or feedstuff having an immunopotentiating activity.

The present invention also relates to a medicinal agent or food for regulating a function of the digestive tract or gastrointestine of an animal, including a human being, and a feed or feedstuff having the activity of regulating the function of the digestive tract or gastrointestine of an animal.

Further, the present invention relates to a medicinal agent for improving antibiotic absorption by an animal, including a human being, and a feed or feedstuff for improving antibiotic absorption by an animal.

Furthermore, the present invention relates to a medicinal agent for accelerating an animal growth or for improving an egg production rate, egg weight, egg quality or eggshell strength of an animal and a feed or feedstuff having the activity of accelerating an animal growth or the activity of improving an egg production rate, egg weight, egg quality or eggshell strength of an animal.

2. Description of the Related Art

With the recent progress in immunology, it has come to be thought that the various maladies and infectious diseases of an animal, including a human being, are caused by a weakening or deficiency in the immune system of the animal.

For example, a human being frequently suffers from a weakening or deficiency in his immune system because of bronchial asthma, allergic diseases, articular rheumatism, autoimmune diseases, nutritional disorders, surgical operation, aging, cancer, organ transplantation, pregnancy or the like, resulting in the complication of an infectious disease such as respiratory infections, sepsis or urinary infections.

Up to this time, various antibiotics have been administered to patients with such maladies or infectious diseases. Meanwhile, large-scale or overcrowded raising has been employed in the fields of animal husbandry and aquaculture in order to raise livestock, poultries or fish efficiently, and in such raising, it has been also a practice to administer a high dose of an antibiotic.

The repeated administration of an antibiotic for a long period causes the generation of antibiotic-resistant bacteria to lower the effect of the antibiotic. Further, hospital infection has also become a significant problem. Under these circumstances, it has been expected to develop a preventive and therapeutic agent which can potentiate the immune system while reducing the dosage of an antibiotic.

Further, the overcrowded raising employed in the fields of animal husbandry and aquaculture has a problem in that various infectious diseases frequently break out because of stress or juvenile immuno-deficiency. Furthermore, when a high dose of an antibiotic is administered as a countermeasure against the problem, there occur other problems that the antibiotic is not completely consumed and that antibiotic-resistant bacteria propagate in the environment.

Recently, animals, including human beings, have frequently suffered from various gastrointestinal diseases which are caused by a lowering or deficiency in the immune system, stress, dyspepsia or the like, and most of which are accompanied with diarrhea.

For example, a human being becomes susceptible to an infectious disease of the digestive tract as his resistance lowers, and representative examples of the infectious disease include bacterial, vital and parasitic diarrheas. Further, the above gastro-intestinal diseases also include acute diarrheas caused by food poisoning and food allergy and chronic diarrheas caused by a disorder of digestion and absorption, excess gut hormone and colic diseases.

It has been the practice to administer an intestinal depressomotor for the intestines, an astringent, an irritant-absorbing agent, a torpent for enteric mucous membranes or various antibiotics against these gastrointestinal diseases.

Meanwhile, large-scale or overcrowded raising has been employed in the fields of animal husbandry and aquaculture to raise livestock, poultries or fish efficiently. In such raising, it has been a practice to administer the above therapeutic agents for the treatment of diarrhea caused by stress or dyspepsia. Particularly, a large amount of an antibiotic has been used for the prevention of infectious diseases.

The administration of the above depressomotor or astringent is essentially a nosotropic means, while that of an antibiotic is an etiotropic one. However, the repeated administration of an antibiotic for the prevention of infectious diseases has a problem that the preventive effect lowers owing to the generation of antibiotic-resistant bacteria.

Under these circumstances, it has been expected to develop a novel preventive and therapeutic agent which can regulate gastrointestinal functions themselves and is safe.

Up to this time, various antibiotics have been administered to patients with various maladies or infectious diseases. Meanwhile, large-scale or overcrowded raising has been employed in the fields of animal husbandry and aquaculture to raise livestock, poultries or fish efficiently. In such raising, it has been a practice to administer a high dose of an antibiotic.

With respect to the use of an antibiotic, however, there have been pointed out problems such that the antibiotic accumulates in the body of an animal to affect the body and that the administration of a more potent antibiotic becomes necessary because of the generation of antibiotic-resistant bacteria. Further, the administration of an antibiotic to an animal is problematic also in that the environment is polluted with the antibiotic contained in the excrement of the animal. Under these circumstances, it has been expected that the dose of the antibiotic to be administered is reduced. In order to reduce the dose of the antibiotic, it has been believed effective that the absorption of the antibiotic through the digestive tract should be enhanced to attain an effect equal or superior to that attained by the administration thereof in a high dose, even when the antibiotic is administered in a low dose. However, no substance which can improve the absorption of an antibiotic has been found as yet.

In preparing animal feed, various attempts have been widely made at improving the feeding efficiency for animals and also at accelerating the growth thereof by adding various antibiotics to the feed, incorporating an increased amount of proteins into the feed, changing the feeding method or improving the dosage form of the feed.

With respect to the use of an antibiotic, however, there have been pointed out problems such that the antibiotic remains or accumulates in the body of an animal to affect the body and that the administration of a more potent antibiotic becomes necessary because of the generation of resistant bacteria. Further, the administration of an antibiotic to an animal is problematic also in that the environment is polluted with the antibiotic contained in the excrement of the animal. In addition, the effects obtained by varying the feeding method and the dosage form of the feed are limited. Under these circumstances, it is necessary to develop a safe and less problematic animal growth accelerator, feed and improver for the egg production ratio, egg weight, egg quality or eggshell strength of animals.

DISCLOSURE OF THE INVENTION

Summary of the Invention

In view of the above problems, the present inventors have extensively studied for many years and have found that *Rosa roxburghii*, *Artemisiae argyi folium* and *Brassica oleracea* var. capitata L. are useful for overcoming the problems. The present invention has been accomplished on the basis of this finding.

Thus, the present invention provides;

(1) a pharmaceutical composition comprising a pharmaceutically effective amount of a substance selected from the group consisting of *Rosa roxburghii*, *Artemisiae argyi folium* and *Brassica oleracea* var. capitata L. and a pharmaceutically acceptable carrier;

(2) a pharmaceutical composition comprising a pharmaceutically effective amount of a substance selected from the group consisting of *Rosa roxburghii*, *Artemisiae argyi folium* and Brassica *oleracea* var. capitata L.;

(3) a feedstuff for an animal comprising a substance selected from the group consisting of *Rosa roxburghii, Artemisiae argyi folium* and *Brassica oleracea* var. capitata L.;

(4) a feedstuff for an animal comprising a substance selected from the group consisting of *Rosa roxburghii, Artemisiae argyi folium* and *Brassica oleracea* var. capitata L. and a basal diet;

(5) a method for feeding a feedstuff comprising a substance selected from the group consisting of *Rosa roxburghii, Artemisiae argyi folium* and *Brassica oleracea* var. capitata L. to an animal; and (6) a method for feeding a feedstuff comprising a substance selected from the group consisting of *Rosa roxburghii, Artemisiae argyi folium* and *Brassica oleracea* var. capitata L. and a basal diet to an animal.

In view of the above problems with respect to the use of antibiotics, the present inventors have extensively studied for many years on protective agents which are safe for animals and have found that *Rosa roxburghii, Artemisiae argyi folium* and *Brassica oleracea* var. capitata L. have an immunopotentiating activity. The present invention has been accomplished on the basis of this finding.

Thus, the present invention provides;

(7) a method for immunopotentiating and protecting from infectious diseases, which comprises administering a pharmacologically effective amount of a substance selected from the group consisting of *Rosa roxburghii, Artemisiae argyi folium* and *Brassica oleracea* var. capitata L. to an animal;

(8) a use of a substance selected from the group consisting of *Rosa roxburghii, Artemisiae argyi folium* and *Brassica oleracea* var. capitata L. for preparing a medicine for an animal for immunopotentiating and protecting from infectious diseases;

(9) a use of a substance selected from the group consisting of *Rosa roxburghii, Artemisiae argyi folium* and *Brassica oleracea* var. capitata L. for immunopotentiating and protecting from infectious diseases in an animal;

(10) a pharmaceutical composition for immunopotentiating and protecting from infectious diseases in an animal, comprising a pharmaceutically effective amount of a substance selected from the group consisting of *Rosa roxburghii, Artemisiae argyi folium* and *Brassica oleracea* var. capitata L. and a pharmaceutically acceptable carrier;

(11) a medicinal agent for immunopotentiating and protecting from infectious diseases of an animal, comprising a substance selected from the group consisting of *Rosa roxburghii, Artemisiae argyi folium* and *Brassica oleracea* var. capitata L. and a pharmaceutically acceptable carrier; and

(12) a feedstuff for an animal, which is useful for immunopotentiating and protecting from infectious diseases in an animal, comprising a substance selected from the group consisting of *Rosa roxburghii, Artemisiae argyi folium* and *Brassica oleracea* var. capitata L.

In view of the above problem, the present inventors have extensively studied for many years regulating agents for the digestive tract which are safe for human beings and animals, and have found that *Rosa roxburghii, Artemisiae argyi folium* and *Brassica oleracea* var. capitata L. have the activity of regulating gastrointestinal functions. The present invention has been accomplished on the basis of this finding.

Thus, the present invention provides;

(13) a method for regulating the digestive tract, which comprises administering a pharmacologically effective amount of a substance selected from the group consisting of *Rosa roxburghii, Artemisiae argyi folium* and *Brassica oleracea* var. capitata L. to an animal;

(14) a use of a substance selected from the group consisting of *Rosa roxburghii, Artemisiae argyi folium* and *Brassica oleracea* var. capitata L. for preparing a medicine for an animal for regulating the digestive tract;

(15) a use of a substance selected from the group consisting of *Rosa roxburghii, Artemisiae argyi folium* and *Brassica oleracea* var. capitata L. for regulating the digestive tract of an animal;

(16) a pharmaceutical composition for regulating the digestive tract of an animal, comprising a pharmaceutically effective amount of a substance selected from the group consisting of *Rosa roxburghii, Artemisiae argyi folium* and *Brassica oleracea* var. capitata L. and a pharmaceutically acceptable carrier;

(17) a medicinal agent for regulating the digestive tract of an animal, comprising a substance selected from the group consisting of *Rosa roxburghii, Artemisiae argyi folium* and *Brassica oleracea* var. capitata L. and a pharmaceutically acceptable carrier; and

(18) a feedstuff for an animal, which is useful for regulating the digestive tract of the animal, comprising a substance selected from the group consisting of *Rosa roxburghii, Artemisiae argyi folium* and *Brassica oleracea* var. capitata L.

To provide an absorbefacient which enables a reduction in the dose of an antibiotic when administered together with the antibiotic, the present inventors have extensively studied to find out that the absorption of an antibiotic can surprisingly be improved when *Rosa roxburghii* alone or two or more members selected from among *Rosa roxburghii, Arte-*

*misiae argyi folium* and *Brassica oleracea* var. capitata L. are administered simultaneously with the antibiotic or before or after the administration of the antibiotic.

Thus, the present invention provides;

(19) a method for improving antibiotic absorption, which comprises administering a pharmacologically effective amount of a substance selected from the group consisting of *Rosa roxburghii, Artemisiae argyi folium* and *Brassica oleracea* var. capitata L. to an animal;

(20) a use of a substance selected from the group consisting of *Rosa roxburghii, Artemisiae argyi folium* and *Brassica oleracea* var. capitata L. for preparing a medicine for an animal for improving its antibiotic absorption;

(21) a use of a substance selected from the group consisting of *Rosa roxburghii, Artemisiae argyi folium* and *Brassica oleracea* var. capitata L. for improving antibiotic absorption in an animal;

(22) a pharmaceutical composition for improving antibiotic absorption in an animal, comprising a pharmaceutically effective amount of a substance selected from the group consisting of *Rosa roxburghii, Artemisiae argyi folium* and *Brassica oleracea* var. capitata L. and a pharmaceutically acceptable carrier;

(23) a medicinal agent for improving antibiotic absorption in an animal, comprising a substance selected from the group consisting of *Rosa roxburghii, Artemisiae argyi folium* and *Brassica oleracea* var. capitata L. and a pharmaceutically acceptable carrier; and

(24) a feedstuff for an animal, which is useful for improving antibiotic absorption in the animal, comprising a substance selected from the group consisting of *Rosa roxburghii, Artemisiae argyi folium* and *Brassica oleracea* var. capitata L.

To provide a feedstuff free from the abovementioned defects of an ordinary feedstuff and a method of administering the feedstuff to animals, the present inventors have extensively studied. As a result, they have found that the growth of animals, including fetuses, is surprisingly accelerated by administering *Rosa roxburghii* alone or two or more members selected from among *Rosa roxburghii, Artemisiae argyi folium* and *Brassica oleracea* var. capitata L. to them. The inventors have further found that an improvement in the egg production rate, egg weight, egg quality or eggshell strength of birds and fishes is also accelerated by them.

Thus, the present invention provides;

(25) a method for accelerating growth of an animal, which comprises administering a pharmacologically effective amount of a substance selected from the group consisting of *Rosa roxburghii, Artemisiae argyi folium* and *Brassica oleracea* var. capitata L. to the animal;

(26) a use of a substance selected from the group consisting of *Rosa roxburghii, Artemisiae argyi folium* and *Brassica oleracea* var. capitata L. for preparing a medicine for an animal for accelerating growth of the animal;

(27) a use of a substance selected from the group consisting of *Rosa roxburghii, Artemisiae argyi folium* and *Brassica oleracea* var. capitata L. for accelerating growth of an animal;

(28) a pharmaceutical composition for accelerating the growth of an animal, comprising a pharmaceutically effective amount of a substance selected from the group consisting of *Rosa roxburghii, Artemisiae argyi folium* and *Brassica oleracea* var. capitata L. and a pharmaceutically acceptable carrier;

(29) a medicinal agent for accelerating the growth of an animal, comprising a substance selected from the group consisting of *Rosa roxburghii, Artemisiae argyi folium* and *Brassica oleracea* var. capitata L. and a pharmaceutically acceptable carrier;

(30) a feedstuff for an animal, which is useful for accelerating the growth of the animal, comprising a substance selected from the group consisting of *Rosa roxburghii, Artemisiae argyi folium* and *Brassica oleracea* var. capitata L.;

(31) a method for improving an egg production rate, egg weight, egg quality or eggshell strength of an animal, which comprises administering a pharmacologically effective amount of a substance selected from the group consisting of *Rosa roxburghii, Artemisiae argyi folium* and *Brassica oleracea* var. capitata L. to the animal;

(32) a use of a substance selected from the group consisting of *Rosa roxburghii, Artemisiae argyi folium* and *Brassica oleracea* var. capitata L. for preparing a medicine of an animal for improving an egg production rate, egg weight, egg quality or eggshell strength of the animal;

(33) a use of a substance selected from the group consisting of *Rosa roxburghii, Artemisiae argyi folium* and *Brassica oleracea* var. capitata L. for improving an egg production rate, egg weight, egg quality or eggshell strength of an animal;

(34) a pharmaceutical composition for improving an egg production rate, egg weight, egg quality or eggshell strength of an animal, comprising a pharmaceutically effective amount of a substance selected from the group consisting of *Rosa roxburghii, Artemisiae argyi folium* and *Brassica oleracea* var. capitata L. and a pharmaceutically acceptable carrier;

(35) a medicinal agent for improving an egg production rate, egg weight, egg quality or eggshell strength of an animal, comprising a substance selected from the group consisting of *Rosa roxburghii, Artemisiae argyi folium* and *Brassica oleracea* var. capitata L. and a pharmaceutically acceptable carrier; and

(36) a feedstuff for an animal, which is useful for improving an egg production rate, egg weight, egg quality or eggshell strength of the animal, comprising a substance selected from the group consisting of *Rosa roxburghii, Artemisiae argyi folium* and *Brassica oleracea* var. capitata L.

Further scope and applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

*Rosa roxburghii* is a perennial shrub of the family Rosaceae and is native to Guizhou in China and its fruit has been noticed as the material of juice, jam or liquor. The fruit of *Ross roxburghii* has been known to have a pharmacological activity and is useful as an antiulcer agent by virtue of its cancer-preventing, cholesterol level-lowering and antistress activities.

*Artemisiae argyi folium* is a plant of the family Compositae and has been known to be useful as an antidiarrheal or antiabdominalgia agent, a hemostatic or the like. Further, this plant has been known to exhibit a low antimicrobial activity only against Gram-positive bacteria. *Artemisiae argyi folium* includes, for example, *Artemisia princeps* Pampanini, *Artemisia mongolia* Fischer, *Artemisia argyi* LEVL. et VANT., and *Artemisia lavandulaefolia* DC.

*Brassica oleracea* var. capitata L. is a plant of the family Cruciferae and has been used as food.

The *Rosa roxburghii* to be used in the present invention is not particularly limited in form, but may have any form so far as it contains the essences of *Rosa roxburghii*. Generally, the fruit of *Rosa roxburghii* may be used in its raw state or as a dry powder prepared by conventional means prior to use, or an extract prepared by using water, an organic solvent or a mixture of both as an extractant.

The *Artemisiae argyi folium* and *Brassica oleracea* var. capitata L. to be used in the present invention are not particularly limited in form, but may have any form so far as it contains the essences thereof. Generally, the leaf of *Artemisiae argyi folium* or *Brassica oleracea* var. capitata L. may be used in a raw state or as a dry powder prepared by conventional means prior to use, or an extract prepared by using water, an organic solvent or a mixture of both as an extractant.

An extract from the above leaves can be prepared by, e.g., a process which comprises immersing 1 part by weight of the raw material in 5 parts by weight of water, boiling the obtained mixture under heating for 30 minutes to conduct extraction, filtering the resulting system, and concentrating the obtained filtrate to 3.6 parts by weight. The obtained extract may be powdered by spray drying, freeze drying, vacuum drying (vacuum concentration) of the like.

When an organic solvent is used for extraction, methanol, ethanol, n-propanol, n-butanol, acetone, ethyl acetate, ether, methylene chloride, chloroform, benzene, carbon tetrachloride and petroleum ether are preferable. These organic solvents may be used alone or as a mixture of two or more of them.

The extracts thus produced may be used as such or may be concentrated, diluted or freed from the solvent prior to use.

The extract of *Rosa roxburghii* to be used in the present invention may be one commercially available under the trade name of "*Rosa roxburghii* extract powder MF", which is a product of Maruzen Seiyaku K.K. comprising 30% of an extract of *Rosa roxburghii* and 70% of dextrin.

In the present invention, at least one of *Rosa roxburghii*, *Artemisiae argyi folium* and *Brassica oleracea* var. capitata L. is(are) used.

When *Rosa roxburghii* and *Artemisiae argyi folium* are used in the present invention, the ratio between them is not particularly limited. Generally, *Artemisiae argyi folium* is used, in terms of raw leaf, that is, when it is prescribed as the weight of raw leaf, in an amount of 0.25 to 400 parts by weight, preferably 0.5 to 200 parts by weight, still preferably 1 to 100 parts by weight, based on 1 part by weight of the extract of *Rosa roxburghii*.

When both *Artemisiae argyi folium* and *Brassica oleracea* var. capitata L. are used together with *Rosa roxburghii*, the amounts thereof are not particularly limited. Generally, *Artemisiae argyi folium* and *Brassica oleracea* var. capitata L. are used in amounts of 0.25 to 400 parts by weight and 0.5 to 800 parts by weight, respectively, in terms of their respective raw leaf, based on 1 part by weight of the extract of *Rosa roxburghii*. It is preferable that *Artemisiae argyi folium* and *Brassica oleracea* var. capitata L. be used in amounts of 0.5 to 200 parts by weight and 1 to 400 parts by weight respectively, still preferably in amounts of 1 to 100 parts by weight and 5 to 200 parts by weight respectively.

The pharmaceutical composition or the medicinal agent of the present invention may be administered, with the purpose of the prevention of diseases, as a food having a regulating effect on a living body, i.e., a so-called functional food, which can be prepared by adding this composition or agent to food.

When the pharmaceutical composition or the medicinal agent of the present invention comprising one or more members selected from among *Rosa roxburghii*, *Artemisiae argyi folium* and *Brassica oleracea* var. capitata L. is used as a medicine or so-called health food, it may be in the form of tablet, granule, powder, capsule or syrup. The pharmaceutical composition or the medicinal agent is prepared by mixing the members with a conventional filler or carrier, binder, lubricant or the like and treating the obtained mixture in the conventional manner.

When the pharmaceutical composition or the medicinal agent of the present invention comprising one or more members selected from among *Rosa roxburghii*, *Artemisiae argyi folium* and *Brassica oleracea* var. capitata L. is used for an animal, such as a mammal, a bird and a fish, especially for a livestock, the dosage form thereof is not particularly limited. For example, it may be administered to livestock in a state mixed with a basal diet (or feed or feedstuff). That is, this composition or agent may be mixed with a basal diet (or feed or feedstuff) just before using or may be premixed with a basal diet (or feed or feedstuff). In other words, the feedstuff for an animal comprising a substance selected from the group consisting of *Rosa roxburghii*, *Artemisiae argyi folium* and *Brassica oleracea* var. capitata L. of the present invention may be administered to an animal as a feed having a biophylactic and regulating function.

The arbitrary basal diet for animals, which is used for preparing the feed stuff according to the present invention, is not particularly limited. Examples of the raw materials constituting the basal diet include grains such as corn, milo and wheat flour, brans such as defatted rice bran and wheat bran, animal substances such as fish meal and skimmilk. vegetable oil cake such as soybean oil cake, and additives such as calcium carbonate, calcium phosphate, common salt, vitamin $B_2$, DL-methionine, choline chloride, manganese sulfate, dry iron sulfate, calcium iodate, copper sulfate, dry zinc sulfate and sodium saccharin. The basal diet can be prepared by blending some members selected from among these materials. The formulation of the basal diet varies depending upon the animal to which the diet is administered.

The improved feed of the present invention, i.e., the feedstuff containing at least one of *Rosa roxburghii*, *Artemisiae argyi folium* and *Brassica oleracea* var. capitata L. can be administered to various livestock, poultries, pets and fish. The livestock includes pig, cattle, horse, goat, sheep and rabbit; the poultry chicken, Japanese quail, turkey and duck; the pets dog and cat; and the fish yellowtail, sea bream, flatfish, globefish, hardtail, amberjack, salmon, carp, eel, sweetfish, trout, char and lobster.

Needless to say, the pharmaceutical composition, the medicinal agent and the feedstuff of the present invention are non-toxic.

It will next be described when the pharmaceutical composition, the medicinal agent or the feedstuff of the present invention is used for immunopotentiating and protecting from infectious diseases.

In this case, *Rosa roxburghii*, *Artemisiae argyi folium* and *Brassica oleracea* var. capitata L. may be used alone or as a combination of two or more of them. In other words, the combination of *Rosa roxburghii* with *Artemisiae argyi*

*folium*, that of *Rosa roxburghii* with *Brassica olexacea* var. capitata L., that of *Artemisiae argyi folium* with *Brassica oleracea* var. capitata L., and that of *Rosa roxburghii* with *Artemisiae argyi folium* and *Brassica oleracea* var. capitata L. can be used.

*Rosa roxburghii*, *Artemisiae argyi folium* and *Brassica oleracea* var. capitata L. exhibit an immunopotentiating and protective activity even when used each alone. However, the use of a combination of two or more of them surprisingly exhibits an immunopotentiating and protective activity which is higher than that of the use of each of them.

The pharmaceutical composition or the medicinal agent of the present invention can safely and effectively potentiate the immune function of livestock such as cattle, pig or horse, a poultry such as chicken or Japanese quail, fish such as young yellowtail, sea bream, eel, trout, carp or goldfish, a pet such as dog or cat, or a human being to protect the animal or the like from various infectious diseases, which is one of main objects of the present invention.

The term "immunopotentiation" used in this specification means "potentiation of the immune function of an animal such as a human being, a mammal, fish or the like".

The pharmaceutical composition or the medicinal agent of the present invention have the effect of enhancing the immune function of an animal, including a human being, and serves as a preventive and therapeutic pharmaceutical composition or agent for various maladies and infectious diseases by virtue of this effect, so that the diseases against which this composition or agent is efficacious are not particularly limited. For example, it is efficacious against, e.g., articular rheumatism, autoimmune diseases, bronchial asthma, nutritional disorders, surgical operation, diseases of old age and various infectious diseases such as respiratory infection, sepsis and urinary infection with respect to a human being.

With respect to animals other than humans, this composition or agent is efficacious against scours, epizootic pneumonia, atrophic rhinitis and infectious enterogastritis of a pig, pneumonia and Marek's disease of chicken, scours, pneumonia and mastitis of cattle, and AIDS and leukemia of a pet.

Further, with respect to fish, the infectious disease against which the composition or agent of the present invention is efficacious is not particularly limited and includes bacterial diseases such as streptococcosis and nodosity, and viral diseases.

In this case, the dose of *Rosa roxburghii* to be administered varies depending upon the dosage form and the subject animal, so that it is not particularly limited.

For example, an extract of *Rosa roxburghii* is administered to livestock such as a pig in a dose of 25 mg or above, preferably 50 mg or above, still preferably 100 mg or above per kilogram of the body weight.

It will next be described when the pharmaceutical composition, the medicinal agent or the feedstuff of the present invention is used for regulating the digestive tract.

In this case, *Rosa roxburghii* is preferably used as the essential component. The activity of regulating the digestive tract, i.e., the gastrointestinal activity, of the pharmaceutical composition or the medicinal agent is synergistically enhanced when the composition or agent further contains *Artemisiae argyi folium* or *Artemisiae argyi folium* and *Brassica oleracea* var. capitata L. The pharmaceutical composition or the medicinal agent is also used as a component of a feedsuff, and the feedstuff containing the pharmaceutical composition or the medicinal agent also exhibit the above-described gastrointestinal function regulating activity.

The pharmaceutical composition or the medicinal agent of the present invention can efficaciously and safely regulate the function(s) of the digestive tract of livestock such as cattle, pig or horse, poultry such as chicken or Japanese quail, fish such as young yellowtail, sea bream, eel, trout, carp or goldfish, a pet such as a dog or cat, or humans, which is one of the main objects of the present invention.

The term "digestive tract" to be used in this specification refers to the organs ranging from the mouth to the anus, particularly to the stomach, duodenum, small intestine, large intestine and rectum.

The term "function(s) of the digestive tract" or "gastrointestinal function(s)" used in this specification means digestion, absorption and digestive motion such as peristalsis. The pharmaceutical composition or the medicinal agent for the digestive tract according to the present invention is useful as a therapeutic and preventive pharmaceutical composition or agent for diarrhea when it acts on the lower part of the digestive tract, such as the large intestine or rectum, while it is efficacious in alleviating a sharp pain and in moderating gastic emptying and borborygmus when it acts on the upper part thereof, such as the stomach or duodenum.

When the pharmaceutical composition or the medicinal agent for regulating the function(s) of the digestive tract is used as a therapeutic and preventive pharmaceutical composition or agent for diarrhea, it is efficacious against various diarrheas which are not limited in cause and examples of the diarrhea include bacterial diarrhea such as salmonellosis, viral diarrhea such as caused by adenovirus, parasitic diarrhea such as amebic dysentery, toxic diarrhea such as food and drug poisoning, allergic diarrhea caused by, e.g., food allergy, functional diarrheas such as cold diarrhea and neurotic diarrhea, diarrheas caused by the use of an antibiotic (such as one caused by microbial substitution and staphylococcal diarrhea), and chronic diarrheas caused by the disorder of digestion and absorption, excess gut hormone and colic diseases.

With respect to chickens and pigs, the pharmaceutical composition, the medicinal agent or the feedstuff of the present invention is efficacious against bacterial diarrhea such as caused by *Escherichia coli* or swine dysentery, vital diarrhea caused by TGE or rotavirus, or simple diarrhea such as one caused by stress or dietetic diarrhea. Further, it is efficacious also against various diarrheas of fish.

In this case, the dose of *Rosa roxburghii* to be administered varies depending upon the dosage form and the subject animal, so that it is not particularly limited.

For example, an extract of *Rosa roxburghii* is administered to livestock such as a pig in a dose of 20 mg or above, preferably 40 mg or above, still preferably 100 mg or above per kilogram of the body weight.

It will be described about the case that the pharmaceutical composition, the medicinal agent or the feedstuff of the present invention is used for improving antibiotic absorption.

In this case, the pharmaceutical composition or the medicinal agent comprising *Rosa roxburghii* or a combination of two or more members selected from among *Rosa roxburghii*, *Artemisiae argyi folium* and *Brassica oleracea* var. capitata L. is administered simultaneously with an antibiotic or before or after the administration of an antibiotic. As the pharmaceutical composition or the medicinal agent, *Rosa roxburghii*, *Artemisiae argyi folium* and *Bras-*

*sica oleracea* var. capitata L. may be each administered by itself in a raw, dried or pulverized state, or a formulation may be administered. Alternatively, the pharmaceutical composition or the medicinal agent may be added to food or feed in a conventional manner. Namely, the feedstuff comprising a basal diet and at least one of *Rosa roxburghii, Artemisiae argyi folium* and *Brassica oleracea* var. capitata L. of the present invention may be used.

The feedstuff of the present invention is prepared by adding *Rosa roxburghii* or a combination of two or more members selected from among *Rosa roxburghii, Artemisiae argyi folium* and *Brassica oleracea* var. capitata L. to the basal diet described above. The amount of *Rosa roxburghii*, or the combination, is preferably 0.001% by weight or above, still preferably 0.01% by weight or above in terms of the dried extract thereof, i.e., as the weight of the dried extract thereof.

The pharmaceutical composition, the medicinal agent or the feedstuff for improving antibiotic absorption according to the present invention may be administered simultaneously with an antibiotic or, before or after the administration of an antibiotic. In any case, the effect of improving the absorption of an antibiotic can be attained.

In this case, the dose of *Rosa roxburghii* or a combination of two or more members selected from among *Rosa roxburghii Artemisiae argyi folium* and *Brassica oleracea* var. capitata L. is not particularly limited but varies depending upon the dosage form, the subject animal or the dose of the antibiotic.

For example, when the pharmaceutical composition or the medicinal agent for improving antibiotic absorption comprising two or more members selected from among *Rosa roxburghii, Artemisiae argyi folium* and *Brassica oleracea* var. capitata L. is administered to livestock such as a pig as a powdered extract, the powdered extract is administered in an amount of 0.1 part by weight or above, preferably 1 part by weight or above, still preferably 3 parts by weight or above based on 1 part by weight of the antibiotic administered. When *Rosa roxburghii* is administered alone, the amount thereof may be the same as that described above.

It will next be described when the pharmaceutical composition, the medicinal agent or the feedstuff of the present invention is used for accelerating growth of an animal or improving an egg production rate, egg weight, egg quality or eggshell strength.

One of the objects of the present invention is to provide a novel pharmaceutical composition, medicinal agent or feedstuff for accelerating growth of an animal, a novel pharmaceutical composition, medicinal agent or feedstuff for improving the egg production rate, egg weight, egg quality or eggshell strength of animals, and a method for administering them to animals.

More specifically, one of the objects of the present invention is to provide a novel pharmaceutical composition, medicinal agent or feedstuff which can accelerate an increase in the body weight and can improve the survival rate, feed conversion ratio of animals, and a novel pharmaceutical composition, medicinal agent or feedstuff which can improve the survival rate, egg production rate, egg weight, egg quality, eggshell strength and feed conversion ratio of animals.

The term "growth acceleration" or "accelerating growth of an animal" as used herein includes also growth improvement and growth acceleration of fetuses. The expression "improvement in the egg production ratio, egg weight, egg quality and eggshell strength" means an improvement in the egg production ratio, an increase in the egg weight, and improvements in the eggshell and egg quality.

In this case, *Rosa roxburghii* alone or a combination of two or more members selected from among *Rosa roxburghii, Artemisiae argyi folium* and *Brassica oleracea* var. capitata L., preferably a combination of three members described above, as the active ingredient is administered to animals. *Rosa roxburghii, Artemisiae argyi folium* and *Brassica oleracea* var. capitata L. can be administered directly to animals or they can be incorporated in the feedstuff or feed by an ordinary method. Namely, the feedstuff comprising a basal diet and at least one of *Rosa roxburghii, Artemisiae argyi folium* and *Brassica oleracea* var. capitata L. of the present invention may be used.

The feedstuff of the present invention is prepared by adding *Rosa roxburghii* alone or a combination of two or more members selected from among *Rosa roxburghii, Artemisiae argyi folium* and *Brassica oleracea* var. capitata L. to the basal diet described above. The amount of *Rosa roxburghii* or the combination is preferably 0.001% by weight or above, still preferably 0.01% by weight or above in terms of the dried extract thereof, i.e., as the weight of the dried extract thereof.

The pharmaceutical composition, the medicinal agent or the feedstuff accelerates the growth of animals, and improves the rate of raising or feed conversion rate. When it is administered to birds and fishes, it accelerates an improvement in the egg production rate, egg weight, egg quality or eggshell strength of them.

The dose of *Rosa roxburghii* is not particularly limited in this case, since it varies depending on the dosage form thereof and the subject animal.

When *Rosa roxburghii* extract is administered to livestock, such as cattle and pigs, the amount thereof is usually at least 10 mg, preferably at least 50 mg and still preferably at least 100 mg, based on 1 kilogram of the body weight thereof.

EXAMPLES

The present invention will now be described in more detail with reference to the following Examples which should not be considered to limit the scope of the present invention.

In the Examples, the description of the dose of each component, e.g., "10 mg/kg p.o." means oral administration in a dose of 10 mg per kilogram of body weight. Further, the symbols "*" and "**" used in the column of the $x^2$ test in Tables mean $p<0.05$ and $p<0.01$, respectively.

The *Rosa roxburghii* used in Examples A-1, B-1 and B-2 is one commercially available under the trade name of "*Rosa roxburghii* extract powder MF", which is a product of Maruzen Seiyaku K K comprising 30% of an extract of *Rosa roxburghii* and 70% dextrin. The dose of *Rosa roxburghii* is expressed in terms of the weight of this extract powder. The dose of *Actemisiae argyi folium* is expressed in terms of the weight of an extract thereof having 4-fold concentration with respect to its normal weight, while the dose of *Brassica*

*oleracea* var. capitata L. is expressed in terms of the weight of an extract having a 9-fold concentration with respect to its normal weight.

Example A-1

As shown in Tables A-1 and A-2, *Rosa roxburhii*, *Artemisiae argyi folium* and *Brassica oleracea* var. capitata L. were each orally administered alone (Table A-1), or as a mixture of two or more of them (Table A-2), to ten SLC:ICR male mice (age: 5 to 6 weeks, weight: 25 to 33 g) in doses of 500 to 2000 mg/kg, while physiological saline was orally administered thereto as a control. After 24 hours, clinically available *Escherichia coli* ($5.0 \times 10^7$ CFU/mouse, 0.2 ml) was intravenously inoculated into each mouse to determine the survival rate based on the number of viable mice after 7 days from the infection. The results are given in Tables A-1 and A-2.

TABLE A-1

| Sample | Survival rate (%) | $x^2$ test |
|---|---|---|
| control (physiological saline p.o.) | 0 | |
| *Artemisiae argyi folium* 500 mg/Kg p.o. | 20 | |
| *Artemisiae argyi folium* 1000 mg/Kg p.o. | 30 | |
| *Artemisiae argyi folium* 2000 mg/Kg p.o. | 50 | * |
| *Brassica oleracea* var. capitata L. 500 mg/Kg p.o. | 10 | |
| *Brassica oleracea* var. capitata L. 1000 mg/Kg p.o. | 30 | |
| *Brassica oleracea* var. capitata L. 2000 mg/Kg p.p. | 40 | * |
| *Rosa roxburghii* 500 mg/Kg p.o. | 20 | |
| *Rosa roxburghii* 1000 mg/Kg p.o. | 30 | |
| *Rosa roxburghii* 2000 mg/Kg p.o. | 50 | * |

TABLE A-2

| Sample | Survival rate (%) | $x^2$ test |
|---|---|---|
| control (physiological saline p.o.) | 0 | |
| *Artemisiae argyi folium* 500 mg/Kg p.o. and *Brassica oleracea* var. capitata L. 500 mg/Kg p.o. | 40 | * |
| *Artemisiae argyi folium* 1000 mg/Kg p.o. and *Brassica oleracea* var. capitata L. 1000 mg/Kg p.o. | 70 | * |
| *Artemisiae argyi folium* 2000 mg/Kg p.o. and *Brassica oleracea* var. capitata L. 2000 mg/Kg p.o. | 100 | ** |
| *Rosa roxburghii* 500 mg/Kg p.o. and *Artemisiae argyi folium* 500 mg/Kg p.o. | 60 | * |
| *Rosa roxburghii* 1000 mg/Kg p.o. and *Artemisiae argyi folium* 1000 mg/Kg p.o. | 90 | ** |
| *Rosa roxburghii* 2000 mg/Kg p.o. and *Artemisiae argyi folium* 2000 mg/Kg p.o. | 100 | ** |
| *Rosa roxburghii* 500 mg/Kg p.o., *Artemisiae argyi folium* 500 mg/Kg p.o. and *Brassica oleracea* var. capitata L. 500 mg/Kg p.o. | 70 | * |
| *Rosa roxburghii* 1000 mg/Kg p.o., *Artemisiae argyi folium* 1000 mg/Kg p.o. and *Brassica oleracea* var. capitata L. 1000 mg/Kg p.o. | 100 | ** |

As shown in Table A-1, the survival rate increases depending upon the dose of *Rosa roxburghii*, *Artemisiae argyi folium* or *Brassica oleracea* var. capitata L., which reveals that these plants have a protective effect.

As shown in Table A-2, the simultaneous use of *Rosa roxburghii* with *Artemisiae argyi folium*, that of *Artemisiae argyi folium* with *Brassica oleracea* var. capitata L. and that of *Rosa roxburghii* with *Artemisiae argyi folium* and *Brassica oleracea* var. capitata L. exhibit the protective effect exceeding the arithmetic sum of the respective effects of these plants. That is, the above simultaneous use exhibits a significant synergistic effect, being of great value.

The above test in Example A-1 reveals that the medicinal agent for immunopotentiating and protecting from infectious diseases of the present invention has an excellent protective activity against Gram-negative bacteria, which suggests that the agent of the present invention is not one which exhibits a low antimicrobial activity only against Gram-positive bacteria like *Escherichia coli*, but one which potentiates the immune function itself. Accordingly, the agent of the present invention is effective in the prevention and treatment of various maladies and useful as a preventive and therapeutic agent for various infectious diseases or as a functional food or feed. Thus, the present invention is of great value.

Example B-1

As shown in Table B-1, *Rosa roxburghii*, *Artemisiae argyi folium* and *Brassica oleracea* var. capitata L. were each orally administered to six SLC:SD male rats (age: 6 weeks, weight: 250 to 300 g) in a dose of 125 to 500 mg/kg, while physiological saline was orally administered thereto as a control. After 30 minutes, 1 ml of caster oil was further orally administered to the rats to determine the time which elapsed until the occurrence of diarrhea and the total amount of excrement given within 2 hours of the administration. The antidiarrheal index of each case was calculated from these values according to the following formula 1 to evaluate the antidiarrheal activity. The measured values and the antidiarrheal index are given in Table B-1.

$$\frac{\begin{bmatrix} \text{time which has elapsed until} \\ \text{the occurrence of diarrhea} \\ \text{with repsect to fed rat} \end{bmatrix} / \begin{bmatrix} \text{total amount of excrement} \\ \text{with repsect to fed rat} \end{bmatrix}}{\begin{bmatrix} \text{time which has elapsed until} \\ \text{the occurrence of diarrhea} \\ \text{with repsect to control rat} \end{bmatrix} / \begin{bmatrix} \text{total amount of excrement} \\ \text{with repsect to control rat} \end{bmatrix}} = \text{antidiarreal index (which is 1 in case of control rat)}$$

TABLE B-1

| Sample | Time until the occurrence of diarrhea (min) | Total amount of excrement (g) | Anti-diarrheal index |
|---|---|---|---|
| control (physiological saline p.o.) | 38.5 ± 5.9 | 6.7 ± 0.67 | 1.00 |
| Artemisiae argyi folium 125 mg/Kg p.o. | 53.3 ± 13.8 | 4.5 ± 0.83 | 2.06 |
| Artemisiae argyi folium 250 mg/Kg p.o. | 71.8 ± 18.4 | 3.7 ± 1.09 | 3.38 |
| Artemisiae argyi folium 500 mg/Kg p.o. | 95.8 ± 12.8 | 2.0 ± 0.68 | 8.33 |
| Brassica oleracea var. capitata L. 125 mg/Kg p.o. | 45.3 ± 7.9 | 5.9 ± 1.16 | 1.36 |
| Brassica oleracea var. capitata L. 250 mg/Kg p.o. | 49.5 ± 10.7 | 4.7 ± 1.14 | 1.83 |
| Brassica oleracea var. capitata L. 500 mg/Kg p.o. | 51.2 ± 8.2 | 3.8 ± 1.21 | 2.34 |
| Rosa roxburghii 125 mg/Kg p.o. | 50.5 ± 10.0 | 4.2 ± 1.67 | 2.09 |
| Rosa roxburghii 250 mg/Kg p.o. | 68.3 ± 6.4 | 3.7 ± 0.80 | 3.21 |
| Rosa roxburghii 500 mg/Kg p.o. | 77.8 ± 14.4 | 1.8 ± 0.70 | 7.52 |

It was ascertained from the results given in

Table B-1 that *Artemisiae argyi folium*, *Rosa roxburghii* and *Brassica oleracea* var. capitata L. had an antidiarrheal activity.

Example B-2

As shown in Tables B-2 and B-3, two or more members selected from among *Rosa roxburghii*, *Artemisiae argyi folium* and *Brassica oleracea* var. capitata L. were orally administered to six SLC:SD male rats (age: 6 weeks, weight: 250 to 300 g) each in doses of 125 to 500 mg/kg, while physiological saline was orally administered thereto as a control. After 30 minutes, 1 ml of castor oil was further administered orally to the rats to determine the time elapsed until the occurrence of diarrhea and the total amount of the excrement given within 2 hours of the administration. The antidiarrheal index of each case was calculated from these values according to the above formula 1 to evaluate the antidiarrheal activity. The measured values and the antidiarrheal index are given in Tables B-2 and B-3.

TABLE B-2

| Sample | Time until the occurrence of diarrhea (min) | Total amount of excrement (g) | Anti-diarrheal index |
|---|---|---|---|
| control (physiological saline p.o.) | 38.5 ± 5.9 | 6.7 ± 0.67 | 1.00 |
| Artemisiae argyi folium 125 mg/Kg p.o. and Brassica oleracea var. capitata L. 125 mg/Kg p.o. | 62.7 ± 13.4 | 4.2 ± 1.02 | 2.60 |
| Artemisiae argyi folium 250 mg/Kg p.o. and Brassica oleracea var. capitata L. 250 mg/Kg p.o. | 83.5 ± 15.3 | 3.2 ± 1.45 | 4.54 |
| Artemisiae argyi folium 500 mg/Kg p.o. and Brassica oleracea var. capitata L. 500 mg/Kg p.o. | 99.3 ± 13.2 | 1.8 ± 0.70 | 9.59 |
| Rosa roxburghii 125 mg/Kg p.o. and Artemisiae argyi folium 125 mg/Kg p.o. | 78.4 ± 8.6 | 3.5 ± 1.73 | 3.89 |
| Rosa roxburghii 250 mg/Kg p.o. and Artemisiae argyi folium 250 mg/Kg p.o. | 90.3 ± 12.4 | 2.6 ± 1.17 | 6.04 |
| Rosa roxburghii 500 mg/Kg p.o. and Artemisiae argyi folium 500 mg/Kg p.o. | 101.8 ± 14.3 | 1.6 ± 1.58 | 11.06 |

TABLE B-3

| Sample | Time until the occurrence of diarrhea (min) | Total amount of excrement (g) | Anti-diarrheal index |
|---|---|---|---|
| control (physiological saline p.o.) | 38.5 ± 5.9 | 6.7 ± 0.67 | 1.00 |
| Rosa roxburghii 125 mg/Kg p.o., Artemisiae argyi folium 125 mg/Kg p.o. and Brassica oleracea var. capitata L. 125 mg/Kg p.o. | 91.5 ± 17.4 | 3.5 ± 1.73 | 6.37 |
| Rosa roxburghii 250 mg/Kg p.o., Artemisiae argyi folium 250 mg/Kg p.o. and Brassica oleracea var. capitata L. 250 mg/Kg p.o. | 102.0 ± 13.0 | 1.8 ± 0.70 | 9.85 |
| Rosa roxburghii 500 mg/Kg p.o., Artemisiae argyi folium 500 mg/Kg p.o. and Brassica oleracea var. capitata L. 500 mg/Kg p.o. | 110.8 ± 14.0 | 1.3 ± 1.16 | 14.82 |

It has been ascertained from the results given in Tables B-1 and B-2 that the simultaneous use of *Rosa roxburghii* with *Artemisiae argyi folium* exhibits a synergistic antidiarrheal activity, while it has been ascertained from the results given in Tables B-1 and B-3 that the simultaneous use of *Rosa roxburghii* with *Artemisiae argyi folium* and *Brassica oleracea* var. capitata L. also exhibits a synergistic antidiarrheal activity.

The above test in Examples B-1 and B-2 reveals that the medicinal agent for regulating a function of a digestive tract according to the present invention has an excellent antidiarrheal activity. Accordingly, the medicinal agent for regulating a function of a digestive tract of the present invention is effective in the prevention and treatment of diarrhea caused by various diseases, and is useful as a preventive or therapeutic agent for diarrhea or a functional food or feed. Thus, the present invention is of great value.

The mixture of *Rosa roxburghii*, *Artemisiae argyi folium* and *Brassica oleracea* var. capitata L. used in the following Examples C-1, C-2, D-1 to D-6 were prepared as follows:

Raw leaves (3 kg) of *Artemisiae argyi folium* were immersed in 15 l of water and the obtained mixture was boiled for 30 minutes to conduct extraction. The resulting mixture was filtered to recover a filtrate. The filtrate was concentrated to 1.8 kg by heating to give an extract. This extract was powdered by spray drying to give a dry powder of the extract of *Artemisiae argyi folium*. Similarly, *Brassica oleracea* var. capitata L. was also converted into a dry powder of the extract thereof. 1500 g of *Rosa roxburghii* extract powder MF (a product of Maruzen Seiyaku K.K. comprising 30% of an extract of *Rosa roxburghii* and 70% of dextrin) was mixed with 675 g of the above dry powder of the extract of *Artemisiae argyi folium* and 225 g of the above dry powder of the extract of *Brassica oleracea* var. capitata L. to give 2400 g of a mixed powder (a weight ratio of *Rosa roxburghii:Artemisiae argyi folium:Brassica oleracea* var. capitata L. being 2:3:1).

Example C-1

The above mixture of the dry powders or each of the dry powders was orally administered to four SLC:ICR male mice (age: 5 to 6 weeks, weight: 25 to 33 g) in a dose given in Table C-1 together with 10 mg per kilogram of the body weight of amoxicillin (hereinafter referred to simply as "AMPC") as an antibiotic. After 2 hours, blood was gathered from the mice to determine the serum AMPC concentrations, which were compared with those of mice to which AMPC alone had been administered. Each serum AMPC concentration was determined by using a strain of *Sarcina luteas* (Gram-positive and AMPC-sensitive bacterium) according to the disk method (this method of measurement was also employed in Example C-2).

The results are given in Table C-1.

TABLE C-1

| | Serum AMPC concn. μg/ml (figures in parentheses being ratio thereof to the concn. of control) |
|---|---|
| AMPC 10 mg/kg (control) | 2.12 ± 1.14 (1.00) |
| AMPC 10 mg/kg + a mixed powder of *Rosa roxburghii*, *Artemisiae argyi folium* and *Brassica oleracea* var. capitata L. 10 mg/kg | 2.70 ± 1.22 (1.27) |
| AMPC 10 mg/kg + a mixed powder of *Rosa roxburghii*, *Artemisiae argyi folium* and *Brassica oleracea* var. capitata L. 30 mg/kg | 3.04 ± 1.22 (1.43) |
| AMPC 10 mg/kg + a mixed powder of *Rosa roxburghii*, *Artemisiae argyi folium* and *Brassica oleracea* var. capitata L. 90 mg/kg | 3.11 ± 1.97 (1.47) |
| AMPC 10 mg/kg + a mixed powder of *Rosa roxburghii*, *Artemisiae argyi folium* and *Brassica oleracea* var. capitata L. 190 mg/kg | 3.53 ± 1.93 (1.67)* |
| AMPC 10 mg/kg + a mixed powder of *Rosa roxburghii*, *Artemisiae argyi folium* and *Brassica oleracea* var. capitata L. 2000 mg/kg | 5.62 ± 0.57 (2.65)** |
| AMPC 10 mg/kg + *Rosa roxburghii* 10 mg/kg | 4.87 ± 1.81 (2.30)** |
| AMPC 10 mg/kg + *Artemisiae argyi folium* 10 mg/kg | 2.95 ± 1.13 (1.39) |
| AMPC 10 mg/kg + *Brassica oleracea* var. capitata L. 10 mg/kg | 2.20 ± 1.11 (1.04) |

As shown in Table C-1, the group of the mice to which AMPC and *Rosa roxburghii* had been administered and the groups of the mice to which AMPC, *Rosa roxburghii*, *Artemisiae argyi folium* and *Brassica oleracea* var. capitata L. had been administered were apparently improved in the absorption of AMPC depending upon the dose thereof as compared with the group of the mice to which AMPC alone and been administered.

Example C-2

AMPC (10 mg/kg) alone or the mixture of AMPC (10 mg/kg) with the mixed dry powder (30 mg/kg) comprising *Rosa roxburghii*, *Artemisiae argyi folium* and *Brassica oleracea* var. capitata L. was administered to six SPF male pigs (age: 1 month, weight: about 15 kg) mixed with a basal diet to gather blood from the pigs after 0.5, 1, 2, 3 and 6 hours. The serum AMPC concentrations of the pigs to which AMPC and the mixed dry powder had been administered were determined and compared with those of the pigs to which AMPC alone had been administered.

The results are given in Table C-2.

The formulation of the above basal diet are given in Table C-3.

TABLE C-2

| | after 0.5 hr | after 1 hr | after 2 hrs | after 3 hrs | after 6 hrs |
|---|---|---|---|---|---|
| AMPC 10 mg/kg (control) | 3.07 ± 1.55 | 6.03 ± 0.80 | 3.71 ± 0.63 | 2.10 ± 0.40 | 0.85 ± 0.75 |
| AMPC 10 mg/kg + a mixed powder of *Rosa roxburghii*, *Artemisiae argyi folium* and *Brassica oleracea* var. capitata L. 30 mg/kg | 6.03 ± 1.49 (1.63)** | 7.81 ± 1.49 (1.30)* | 5.85 ± 0.80 (1.58)** | 3.71 ± 1.41 (1.77)* | 1.74 ± 1.16 (2.05)** | note)
Serum AMPC concentration, μg/ml
The figures in parentheses are the ratios of the serum AMPC concentrations to that of the control.

TABLE C-3

| Administration period Component | Initiation of feeding to 5 weeks of age Amt. (%) | 5 to 7 weeks of age Amt. (%) |
|---|---|---|
| parched wheat | 33.8 | 20.0 |
| glucose | 9.0 | 5.0 |
| sugar | 3.0 | — |
| wheat flour | — | 20.0 |
| yellow corn | — | 23.6 |
| skimmilk powder | 40.0 | 10.0 |
| fish meal | 3.0 | 5.0 |
| soybean oil cake | 3.0 | 9.0 |
| Torula yeast | 2.0 | 2.0 |
| soybean oil | 4.0 | 3.0 |
| common salt | 0.2 | 0.2 |
| tricalcium phosphate | 1.2 | 1.4 |
| mineral mixture | 0.2 | 0.2 |
| vitamin mixture | 0.2 | 0.2 |
| flavor, antibiotic and other feed additives | 0.4 | 0.4 |

As shown in Table C-2, the pigs to which AMPC and the mixed powder had been administered were apparently improved in the absorption of AMPC over a period of 0.5 to 6 hours after the administration as compared with the pigs to which AMPC alone had been administered.

The results of the above tests suggest that the medicinal agent for improving antibiotic absorption and the feedstuff according to the present invention are so efficacious in improving the absorption of an antibiotic that the dose of the antibiotic can be reduced. Accordingly, the present invention is of great value.

Example D-1

40 sound pigs (castrated pigs of about 10 days old; 3.0 to 3.5 kg) were divided into four groups, i.e., three groups each consisting of ten pigs to which the mixed powder comprising *Rosa roxburghii*, *Artemisiae argyi folium* and *Brassica oleracea* var. capitata L. were administered and a control group consisting of ten pigs to which an ordinary basal diet free of *Rosa roxburghii*, *Artemisiae argyi folium* and *Brassica oleracea* var. capitata L. was administered. A feedstuff enriched with the mixed powder of *Rosa roxburghii*, *Artemisiae argyi folium* and *Brassica oleracea* var. capitata L. in amounts of 0.03, 0.1 or 0.3% by weight was administered to the pigs of one of the three groups for 30 days. After 30 days, the intake of the feedstuff and the gain of body weight were determined to calculate the rate of raising and the feed conversion ratio (feedstuff intake/gain of body weight). The results were compared with those of the control group.

The composition of the artificial milk-based basal diet for piglings was as shown in Table D-1.

The results of the groups to which *Rosa roxburghii*, *Artemisiae argyi folium* and *Brassica oleracea* var. capitata L. were administered and the control group were compared with each other. The t-test was conducted for the gain of body weight in the control group and the groups of the present invention. Table D-2 shows the results.

TABLE D-1

| Feeding period Component | Initiation of feeding to 5 weeks of age Amt. (%) | 5 to 7 weeks of age Amt. (%) |
|---|---|---|
| Roast wheat | 33.8 | 20.0 |
| Glucose | 9.0 | 5.0 |
| Sugar | 3.0 | — |
| Wheat flour | — | 20.0 |
| Yellow corn | — | 23.6 |
| Skim milk powder | 40.0 | 10.0 |
| Fish meal | 3.0 | 5.0 |
| Soybean oil cake | 3.0 | 9.0 |
| Torula yeast | 2.0 | 2.0 |
| Soybean oil | 4.0 | 3.0 |
| Common salt | 0.2 | 0.2 |
| Tricalcium phosphate | 1.2 | 1.4 |
| Mineral mixture | 0.2 | 0.2 |
| Vitamin mixture | 0.2 | 0.2 |
| Flavor, antibiotic and other feed additives | 0.4 | 0.4 |

TABLE D-2

| Group | Feedstuff intake (A) (kg/pig) | Gain of body weight (B) (kg/pig) | Feed conversion ratio (A/B) | Rate of raising |
|---|---|---|---|---|
| Test group (0.03%) | 11.24 | 5.3 ± 1.33** | 2.12 | 88.8% |
| Test group (0.1%) | 11.79 | 6.3 ± 1.61** | 1.87 | 93.0% |
| Test group (0.3%) | 12.32 | 5.7 ± 1.04* | 2.16 | 100% |
| Control group | 8.50 | 3.4 ± 1.15 | 2.50 | 81.9% |

The gain of body weight per pig in the groups to which *Rosa roxburghii*, *Artemisiae argyi folium* and *Brassica oleracea* var. capitata L. were administered was larger than that in the control group, and the feed conversion ratio and the rate of raising were increased in the former group.

Example D-2

18 bull Holstein calves of about 7 days old were divided into three groups, i.e., two groups each consisting of six calves to which *Rosa roxburghii*, *Artemisiae argyi folium* and *Brassica oleracea* var. capitata L. were administered and a control group consisting of six calves to which neither of *Rosa roxburghii*, *Artemisiae argyi folium* and *Brassica oleracea* var. capitata L. was administered. The mixed powder of *Rosa roxburghii*, *Artemisiae argyi folium* and *Brassica oleracea* var. capitata L. was mixed into a milk substitute for raising suckling calves and into a feedstuff containing a milk substitute (artificial milk) for raising suckling calves in an amount of 0.125 or 0.25% by weight based on the basal diet. The milk substitute or the feedstuff was repeatedly administered for 20 days. The dose of the mixed powder was 2.5 g/day or 5 g/day per calf. Each calf was weighed at the beginning of the test and after the completion of the test (after 20 days) to calculate the gain of body weight and the rate of body weight gain per day.

The composition of the feedstuff containing the milk substitute for raising suckling calves was as shown in Table D-3.

The results of the groups to which *Rosa roxburghii*, *Artemisiae argyi folium* and *Brassica oleracea* var. capitata L. were administered and those of the control group are compared with each other. The t-test was conducted in the control group and the groups of the present invention.

Table D-4 shows the results.

TABLE D-3

| Component | Amt. (%) |
|---|---|
| Skim milk powder | 60.0 |
| Dry whey | 14.8 |
| Animal fat or oil | 20.0 |
| Fish soluble | 4.0 |
| Vitamin mixture | 0.5 |
| Mineral mixture | 0.7 |

TABLE D-4

| Group | Gain of body weight (kg/calf) | Gain of body weight (kg/calf/day) |
|---|---|---|
| Test group 2.5 g/day | 41.0 ± 7.45** | 2.05 ± 0.29** |
| Test group 5.0 g/day | 42.5 ± 5.69** | 2.13 ± 0.27** |
| Control group | 25.7 ± 8.32 | 1.29 ± 0.36 |

The gain of body weight per day in the groups to which *Rosa roxburghii, Artemisiae argyi folium* and *Brassica oleracea* var. capitata L. were administered was larger than that in the control group, and the rate of body weight gain was increased in the former group.

Example D-3

80 pullet broilers (chunky) were divided into two groups, i.e., a group consisting of 40 broilers to which *Rosa roxburghii, Artemisiae argyi folium* and *Brassica oleracea* var. capitata L. were administered and a control group consisting of 40 broilers to which neither of *Rosa roxburghii, Artemisiae argyi folium* and *Brassica oleracea* var. capitata L. was administered.

The mixed powder of *Rosa roxburghii, Artemisiae argyi folium* and *Brassica oleracea* var. capitata L. was administered in an amount of 0.1% by weight based on the basal diet for broilers to the group, to which *Rosa roxburghii, Artemisiae argyi folium* and *Brassica oleracea* var. capitata L. were administered, for 6 weeks. Each broiler was weighed at the beginning of the test and after 6 weeks. The average gain of body weight in the group to which *Rosa roxburghii, Artemisiae argyi folium* and *Brassica oleracea* var. capitata L. were administered and that in the control group were calculated.

The composition of the basal diet for broilers was as shown in Table D-5.

The results of the group to which *Rosa roxburghii, Artemisiae argyi folium* and *Brassica oleracea* var. capitata L. were administered and those of the control group are compared with each other. The $x^2$-test for the average gain of body weight was conducted in the control group and the group to which *Rosa roxburghii, Artemisiae argyi folium* and *Brassica oleracea* var. capitata L. were administered.

Table D-6 shows the results.

TABLE D-5

| Feeding period Component | Initiation of feeding to 3 weeks of age Amt. (%) | 3 to 5 weeks of age Amt. (%) | 5 to 6 weeks of age Amt. (%) |
|---|---|---|---|
| Corn | 50.45 | 55.30 | 55.34 |
| Milo | 10.0 | 15.0 | 15.01 |
| Soybean oil cake | 18.0 | 13.0 | 13.01 |
| Rapeseed oil cake | — | 2.5 | 2.51 |
| Fish meal | 8.0 | 5.0 | 5.01 |
| Fish soluble | 2.0 | — | — |
| Absorbent feed | 3.0 | — | — |
| Gluten meal | | | |
| Alfalfa meal | 2.0 | — | — |
| Torula yeast | 1.0 | — | — |
| Meat/bone meal | — | 3.0 | 3.0 |
| Raw rice bran | — | 2.0 | 2.0 |
| Animal fat or oil | 3.3 | 2.8 | 2.81 |
| Common salt | 0.25 | 0.25 | 0.25 |
| Calcium carbonate | 0.6 | 0.3 | 0.30 |
| Dicalcium phosphate | 0.8 | 0.5 | 0.5 |
| Lysine | — | — | — |
| Methionine | 0.18 | — | — |
| Vitamin mixture | 0.1 | 0.1 | 0.1 |
| Choline chloride | 0.05 | 0.06 | 0.06 |
| Mineral mixture | 0.1 | 0.1 | 0.1 |
| Flavor, antibiotic and other feed additives | 0.17 | 0.09 | — |

TABLE D-6

| Group | Av. body wt. at initiation of feeding (g/broiler) | Av. body wt. after 6 weeks (g/broiler) | Av. gain of body weight (g/broiler) |
|---|---|---|---|
| Test group (0.1%) | 43.8 ± 0.08 | 2065 ± 8.7 | 2021.7 ± 8.6** |
| Control group | 43.6 ± 0.07 | 1879 ± 10.2 | 1835.4 ± 10.1 |

The increase in the average body weight in the group to which *Rosa roxburghii, Artemisiae argyi folium* and *Brassica oleracea* var. capitata L. were administered was larger than that in the control group.

Example D-4

12,000 young yellowtails having an average body weight of about 600 g were divided into two groups, i.e., a group consisting of 6,000 young yellowtails to which *Rosa roxburghii, Artemisiae argyi folium* and *Brassica oleracea* var. capitata L. were administered and a control group consisting of 6,000 young yellowtails to which neither of *Rosa roxburghii, Artemisiae argyi folium* and *Brassica oleracea* var. capitata L. was administered. The mixed powder of *Rosa roxburghii, Artemisiae argyi folium* and *Brassica oleracea* var. capitata L. were mixed with a basal diet for young yellowtails (Moist pellets) in an amount of 0.5% by weight based on the basal diet and the resultant mixture was administered to them at intervals of three days for one month. The results were compared with those of the control group. The young yellowtails were raised in a crawl having a size of about 3 m×3 m×3 m. During the test period, the feedstuff was administered once a day in an amount of about 3% by weight based on the body weight a day.

The composition of the basal diet for young yellowtails was as shown in Table D-7.

The death rate during the test period in the group to which *Rosa roxburghii, Artemisiae argyi folium* and *Brassica*

*oleracea* var. capitata L. were administered and that in the control group were compared with each other to evaluate the effect of improving the rate of raising. The $x^2$-test was conducted in the control group and the group of the present invention.

The results are given in Table D-8.

TABLE D-7

| Component | Amt. (%) |
|---|---|
| Fish meal | 56.0 |
| Meat/bone meal | 3.0 |
| Soybean oil cake | 5.0 |
| Corn gluten meal | 3.0 |
| Torula yeast | 2.0 |
| Wheat flour | 28.4 |
| Vitamin mixture | 1.0 |
| Choline chloride | 0.3 |
| Inorg. mixture | 1.0 |
| Sodium polyacrylate | 0.3 |

TABLE D-8

| Group | No. of samples (fish) | No. of died samples (fish) |
|---|---|---|
| Test group (0.1%) | 6000 | 180** |
| control group | 6000 | 750 |

The death rate during the test period in the group to which *Rosa roxburghii*, *Artemisiae argyi folium* and *Brassica oleracea* var. capitata L. were administered was far smaller than that in the control group to prove the effect of improving the rate of raising.

Example D-5

0.01, 0.03 or 0.10%, based on the amount of the mixed extract powder comprising *Rosa roxburghii*, *Artemisiae argyi folium* and *Brassica oleracea* var. capitata L. used in a pellet for mice and rats, of a preparation prepared by spraying an aqueous suspension of the mixed extract powder followed by drying, was used to form the pellet for mice and rats. Each feedstuff containing *Rosa roxburghii*, *Artemisiae argyi folium* and *Brassica oleracea* var. capitata L. thus prepared was administered to each group of male slc:SD rats, which consisted of 8 rats of 21 days old (body weight: 50 to 57 g), for one month and then each rat was weighed to calculate the rate of body weight gain.

The composition of the basal diet for rats (pellet) was as shown in Table D-9.

The body weights of the rats weighed during the test period in the group to which *Rosa roxburghii*, *Artemisiae argyi folium* and *Brassica oleracea* var. capitata L. were administered were compared with those in the control group to examine the effect on the gain of body weight in both groups. The t-test was conducted in the control group and the groups to which *Rosa roxburghii*, *Artemisiae argyi folium* and *Brassica oleracea* var. capitata L.

The results are given in Table D-10

TABLE D-9

| Component | Amt. (%) |
|---|---|
| Casein | 14.12 |
| Corn starch | 58.40 |
| Glucose | 12.83 |

TABLE D-9-continued

| Component | Amt. (%) |
|---|---|
| Soybean oil | 5.45 |
| Cellulose | 5.00 |
| Minerals | 4.00 |
| Vitamins A and D | 0.10 |
| Vitamin B | 0.10 |

TABLE D-10

Average body weight (g) and rate of body weight gain in each group

| Group | 0 week | 1 week | 2 weeks | 3 weeks | 4 weeks |
|---|---|---|---|---|---|
| Test group (0.03%) | 52.9 ± 1.48 (1.00) | 106.7 ± 4.29 (2.02) | 162.4 ± 7.17 (3.06) | 213.4 ± 6.95 (4.03) | 258.2 ± 7.70 (4.86)* |
| Test group (0.1%) | 53.2 ± 1.83 (1.00) | 107.6 ± 3.77 (2.02) | 162.6 ± 7.28 (3.06) | 216.3 ± 9.41 (4.07) | 258.5 ± 10.96 (4.88)* |
| Test group (0.3%) | 53.7 ± 2.65 (1.00) | 107.6 ± 3.23 (2.00) | 166.7 ± 6.09 (3.10) | 221.4 ± 10.61 (4.12) | 270.2 ± 12.53 (5.03)** |
| Control group | 53.8 ± 1.38 (1.00) | 102.9 ± 5.23 (1.91) | 157.3 ± 9.91 (2.92) | 204.5 ± 13.41 (3.80) | 241.9 ± 17.08 (4.50) |

After the administration of *Rosa roxburghii*, *Artemisiae argyi folium* and *Brassica oleracea* var. capitata L., an increment in the rate of body weight gain of 0.23 to 0.53 was recognized depending on the dose, as compared with the control group.

Example D-6

The tests were conducted twice by using groups of Dekalb-TX chickens of 182 days old (average body weight: 1.5 kg). Each group consisted of 8 chickens. The average results are given in Table D-11 and D-12. In the test, the chickens were divided into three groups, i.e., a group to which 0.03% of the mixed powder of *Rosa roxburghii*, *Artemisiae argyi folium* and *Brassica oleracea* var. capitata L. was administered, a group to which 0.1% of the mixed powder was administered, and the control group. The feeding was conducted for a period of 18 days.

After the completion of the feeding, body weight and egg weight determination, egg quality test and eggshell strength determination (with an eggshell strength meter) were conducted. Further, the feed conversion ratio (feedstuff intake/gain of body weight) was calculated.

The results are given in Tables D-11 and D-12.

TABLE D-11

| Group | Egg prodn. rate | Egg weight/day (g/chicken · day) | Feed conversion ratio |
|---|---|---|---|
| Test group (0.03%) | 79.7% | 47.3 | 2.14 |
| Test group (0.1%) | 79.3% | 46.6 | 2.28 |
| Control group | 74.2% | 44.2 | 2.34 |

Note)
Egg weight/day indicates the total weight of eggs laid by a chicken a day.

TABLE D-12

| Group | Eggshell strength (kg/cm$^2$) | Eggshell thickness (mm) | Eggshell (wt. %) |
| --- | --- | --- | --- |
| Test group (0.03%) | 3.40 | 0.358 | 10.6 |
| Test group (0.1%) | 3.16 | 0.359 | 10.4 |
| Control group | 3.12 | 0.374 | 10.5 |

It will be apparent from Table D-11 that the egg production rate, egg weight and feed conversion ratio were increased more remarkably in the group to which *Rosa roxburghii, Artemisiae argyi folium* and *Brassica oleracea* var. capirate L. had been administered than those in the control group.

It will be apparent from Table D-12 that as compared with the thickness of the eggshell, the eggshell strength was more increased in the group to which *Rosa roxburghii, Artemisiae argyi folium* and *Brassica oleracea* var. capitata L. had been administered than that in the control group. The results promise the prevention of egg cracking.

One embodiment of the present invention provides a medicinal agent or animal feedstuff for accelerating growth of an animal which comprises *Rosa roxburghii* alone or *Rosa roxburghii, Artemisiae argyi folium* and *Brassica oleracea* var. capitata L. to be administered to animals directly or as additives to be incorporated into a basal diet so as to improve the body weight gain, survival rate and feed conversion ratio of an animal; and another embodiment of the present invention provides a medicinal agent for improving an egg production rate, egg weight, egg quality or eggshell strength of animals. Since *Rosa roxburghii, Artemisiae argyi folium* and *Brassica oleracea* var. capitata L. are used, a high degree of safety is afforded and no environmental pollution is caused. Further, *Rosa roxburghii, Artemisiae argyi folium* and *Brassica oleracea* var. capitata L. are available at low costs and are excellent as a medicinal agent or animal feedstuff for accelerating growth of an animal and a medicinal agent for improving an egg production rate, egg weight, egg quality or eggshell strength of an animal and have a high storageability.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What we claim is:

1. A method for immunopotentiating and protecting an animal from an infection caused by *Escherichia coli*, which comprises administering a pharmaceutically effective amount of a mixture of *Rosa roxburghii, Artemisiae argyi folium* and *Brassica oleracea* var. capitata L. to the animal.

2. The method of claim 1, wherein said infection is selected from the group consisting of a respiratory infection, sepsis and a urinary infection.

3. The method for immunopotentiating and protecting from an infection according to claim 1, wherein the mixture is an extract thereof.

4. The method for immunopotentiating and protecting from an infection according to claim 1, wherein the animal is a mammal.

5. The method for immunopotentiating and protecting from an infection according to claim 4, wherein the mammal is a human.

* * * * *